United States Patent [19]

Batchelor

[11] 4,391,365
[45] Jul. 5, 1983

[54] SINGLE DISPENSING MULTIPLE SUTURE PACKAGE

[75] Inventor: Jay A. Batchelor, Bethel, Conn.

[73] Assignee: American Cyanamid Company, Stamford, Conn.

[21] Appl. No.: 262,159

[22] Filed: May 11, 1981

[51] Int. Cl.³ .................................................. A61L 17/02
[52] U.S. Cl. ..................... 206/63.3; 206/227; 206/363; 206/380; 206/485; 229/75; 229/92.7
[58] Field of Search ..................... 206/63.3, 523, 380, 206/381, 382, 370, 227, 363, 485; 229/75, 87 R, 88, 92.1, 92.3, 92.5, 92.7

[56] References Cited

U.S. PATENT DOCUMENTS

| | | | |
|---|---|---|---|
| 3,759,376 | 9/1973 | Lisowski | 206/63.3 |
| 3,857,484 | 12/1974 | Thyen | 206/227 |
| 3,985,227 | 10/1976 | Thyen et al. | 206/63.3 |
| 4,034,850 | 7/1977 | Mandel et al. | 206/63.3 |
| 4,089,409 | 5/1978 | Cerwin | 206/63.3 |
| 4,120,395 | 10/1978 | Mandel et al. | 206/63.3 |
| 4,135,623 | 1/1979 | Thyen | 206/63.3 |

Primary Examiner—Allan N. Shoap
Assistant Examiner—Jimmy G. Foster
Attorney, Agent, or Firm—Charles F. Costello, Jr.

[57] ABSTRACT

A surgical suture package comprises a center panel. At least one foam receptacle is affixed to the panel. A plurality of cards are placed onto the panel, adjacent to the receptacle. A plurality of sutures are singly contained in a non-tangling configuration on a major portion of each card.

A first flap is placed onto the cards. A means is provided for attaching the first flap to the cards and to the panel. A second flap is foldably attached to the panel, and is placed onto the receptacle and the first flap.

The package is useful for singly containing a plurality of sutures with at least one end of each suture contained by a receptacle.

9 Claims, 6 Drawing Figures

SINGLE DISPENSING MULTIPLE SUTURE PACKAGE

This invention relates to a single dispensing multiple surgical suture package. More specifically, this invention relates to the dispensing of a double armed or single armed needled cardiovascular suture from a suture package containing multiple sutures. The suture package has a center panel and a plurality of cards. A plurality of sutures in series can be singly contained on the center panel and between the cards. This invention can also relate to a process of winding, separating and identifying a plurality of sutures in the suture package, and to a method of securing the suture package for dispensing of each suture. A suture is a strand of material with or without an attached needle or needles used for suturing, ligating or other surgical procedures.

There are many sizes of sutures, and many materials of construction. Such materials can be catgut or polyglycolic acid for absorable sutures. Other materials of construction can be silk, cotton, nylon, polyester, polyethylene, polypropylene, stainless steel and insulated polyester stainless steel. There are also several different needle types in common use such as pointed straight, pointed curved, three cornered straight, three cornered curved, three cornered reverse cutting, regular curved and various types of needles with side cutting edges. The variations and combinations of each suture and of each suture with an attached needle or needles means that the suture manufacturer may supply sutures and/or suture-needle(s) combinations running into the thousands. The importance of positive identification and of efficient, economical packaging can thus be readily appreciated.

In specific types of surgery, for example, cardiovascular surgery, relatively long sutures are required. Also many sutures, e.g. up to about 10 sutures, of the same needle, size, and material are generally required. Finally, double-armed sutures, i.e., sutures with a needle attached to both ends, as well as single-armed sutures, i.e., sutures with a needle attached to an end, are commonly used.

In certain surgical procedures involving the suturing of delicate tissue, particularly in cardiovascular operations, it is customary to provide the suture with a pledget. A pledget is a cushioning pad which prevents the suture from cutting into and through the tissue. A pledget can be composed of homo- or copolymer of a fluorinated hydrocarbon.

The suture package of the present invention has advantages over the prior art suture packages. One advantage is that the sutures are contained in series and in a non-tangling configuration in the suture package. Thus the overall size of the suture package, specifically where the sutures are cardiovascular sutures, has been greatly reduced. A reduction in the size of the suture package is a more efficient use of the suture packaging materials and is a more difficult use of shipping and/or storing space. Another advantage is that at least one end of each suture is contained by the foam receptacle(s). Thus each suture can be relatively quickly and easily dispensed from the package.

Still another advantage is the second flap which is foldably attached to the center panel. Thus the second flap can be rotated onto the external surface of the center panel. The size of the suture package is therefore not increased after the package is opened and during the dispensing of the sutures. A still further advantage is a first contacting means on the internal surface of the second flap. The contacting means allows the suture package to be affixed to a support, e.g., a towel or a stand. Only one hand can be required for dispensing the suture, thus permitting the other hand to perform other functions.

Yet another advantage are numbers which can be located adjacent to at least one end of each suture contained by the foam receptacle(s). Thus the number of sutures contained and/or remaining in the suture package can be easily identified. Also, the foam and number combination can be used for returning used needles to the package for easy accountability and convenient storage.

Still yet another advantage is that each suture and at least one end of each suture is contained in the suture package without the use of mounting, containing or centering lists. Therefore the possibility that the sutures will be damaged, e.g. by fraying or unbraiding or storing, shipping or dispensing is greatly reduced or eliminated.

In use, a pledget is located in about the middle of the suture. The suture package of this invention has advantages over the prior art methods "centering" the pledget. The prior art methods are, e.g., to have the pledget located at the suture end or ends. The user then manually centers the pledget after dispensing the suture from the package. Other methods include suture package centering means, e.g. as disclosed in U.S. Pat. No. 4,034,850 issued July 12, 1977 which is incorporated by reference. The centering means physically centers the pledget during dispensing of the suture from the package. The suture package of this invention allows the pledget to be placed in about the middle of the suture on loading and to remain in about the middle of the suture on dispensing either one end or both ends of the suture.

The suture package of this invention has other advantages over the prior art. For example, in certain surgical procedures, sterile suture packages are placed on a towel, on a towel covered stand or on a stand from dispensing. Larger suture packages, e.g. packages containing cardiovascular sutures, may be placed under the towel to save space. The dispensing of a suture from a package on the towel or stand can require one hand to hold the package and one hand to withdraw the suture. One of the embodiments of the suture package of this invention contains a first contacting means. The contacting means allows the suture package to be affixed to a support, e.g., a towel or a stand. Because the suture package is secured to a support, only one hand can be required for dispensing the suture. Also, because each suture is contained in the suture package in a non-tangling configuration, the size of the package is reduced. Thus, the suture package of this invention containing cardiovascular sutures may but does not have to be placed under a towel to save space.

A surgical suture package has been invented. The package comprises: a center panel; at least one foam receptacle affixed to said panel; a plurality of cards or an accordion folded continuous sheet, placed onto said panel adjacent to said receptacle; a first flap placed onto said cards or sheet; means for attaching said first flap to said cards or sheet, and to said panel; and a second flap foldably attached to said panel and placed onto said receptacle and said first flap, whereby a plurality of sutures in series can be singly contained on said panel and between said cards or sheet with at least one end of each suture contained by said receptacle.

Other embodiments of the package are wherein two foam receptacles are affixed respectively to said panel and to a card; wherein said receptacles are affixed in tandem; wherein said receptacles contain suture mounting means; wherein the internal surfaces of said flaps contain a first contacting means; wherein said first contacting means is a coordinating adhesive strip affixed to said flaps; wherein said second flap is rotated onto the external surface of said panel, whereby said second flap can be affixed to a suture package support by said first contacting means; wherein the external surface of said second flap contains a second contacting means; wherein said second contacting means is a pealable adhesive strip; wherein said second flap is rotated onto the external surface of said panel, whereby said second flap can be affixed to said panel by said second contacting means; wherein said first flap is foldably attached to said panel; wherein the means for attaching said first flap to said panel is a tab on said first flap and a third flap foldably attached to said panel, opposing said first flap and containing a slot, whereby said first flap tab coordinates with said third flap slot; and wherein the means for attaching said first flap to said cards or sheet is a tab on opposing edges of each card or each fold of said sheet and an opening on the opposing edges of said first and third flaps, whereby each tab coordinates with each opening.

Still other embodiments of the package are wherein each suture contained by said receptacle(s) is single armed; wherein a plurality of double armed sutures are singly contained on said panel and between said cards or sheet in a non-tangling configuration, with both ends of each suture contained on a receptacle; wherein a plurality of double armed sutures are singly contained on said panel and between said cards or sheet in a non-tangling configuration with both ends of each suture contained in said suture mounting means; and wherein a pledget is located in about the middle of each suture.

DESCRIPTION OF THE INVENTION

Figure 1:
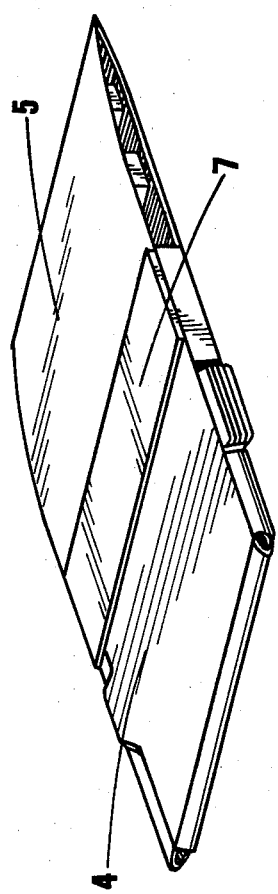
FIG. 1 is a perspective view of a folded suture package of this invention.

The present invention is designed for dispensing of single or double armed sutures from a package containing a multiple of sutures. The package is a sterile compartmented folder containing up to ten sutures, or for certain uses, more than ten sutures, wound in a compact configuration allowing each suture to be grasped by the needle or needles and dispensed independently of the others without tangling.

The package contains a center panel, individual cards or an accordion folded continuous sheet placed onto the center panel, and a first flap placed onto the cards or onto the accordion folded sheet. The continuous sheet contains appropriate cutouts to provide a plurality of tabs when the sheet is accordion folded. The center panel and the cards or the accordon folded sheet separate each individually wound suture. The center panel, cards or accordion folded sheet, first flap, and also second and third flaps to be subsequently described may be composed of paperboard, paper, plastic or any combination of these materials.

Each suture is wound in a non-tangling configuration, for example a helical, coil or figure eight configuration, on the center panel, and on the cards or the accordion folded sheet. Each suture can be wound manually. To assist in the manual winding, a fixture containing winding pins can be used. The winding pins are placed through openings in the center panel, and through coordinating openings in the cards or in the accordion folded sheet. The openings are shown but not described in FIGS. 2 to 5. The wound suture is then separated from the next suture with a card or an accordion folded continuous sheet to prevent tangling of the sutures during dispensing. If each suture is wound with a pledget, the pledget is centered on the suture. This allows the suture to be withdrawn using one or both needles with the pledget in the center and thus eliminates the need for the surgeon to center the pledget after dispensing.

At least one foam receptacle is attached to the center panel to provide secure, protective needle placement. The needles are placed slightly separated in the foam or in suture mounting slits contained in the foam, enabling one or both needles to be grasped by a hand or with a needle holder. The foam is manufactured from a commercially available polyolefin foam, such as polyethylene or polypropylene. Optionally, numbers can be located next to the foam, for example to assist in locating the sutures and/or to verify the number of sutures contained in the package.

A first contacting means, for example a pressure sensitive or adhesive tape is affixed to the internal surface of a second flap foldably attached to the center panel. The second flap is placed onto the receptacle and the first flap. The first contacting means secures the second flap to the first flap. A second contacting means is affixed to the external surface of the second flap.

On rotating the second flap onto the external surface of the center panel, the second flap can be affixed to a suture package support by the first contacting means. On rotating the second flap onto the external surface of the center panel, the second flap can be affixed to the center panel.

FIG. 1 describes the preferred suture package. The package can be contained in a sealed envelope, for example as described in U.S. Pat. No. 4,089,410 FIG. 1 numeral 31 which is incorporated by reference. Preferably, the exterior envelope is composed of a gas pervious, bacteria-impervious spun bonded backing and transparent facing. A label showing product information such as the type, size, and/or length of the suture and/or of the needles, and the manufacturer can be affixed to an exterior flap, for example flap 4.

Figure 3:
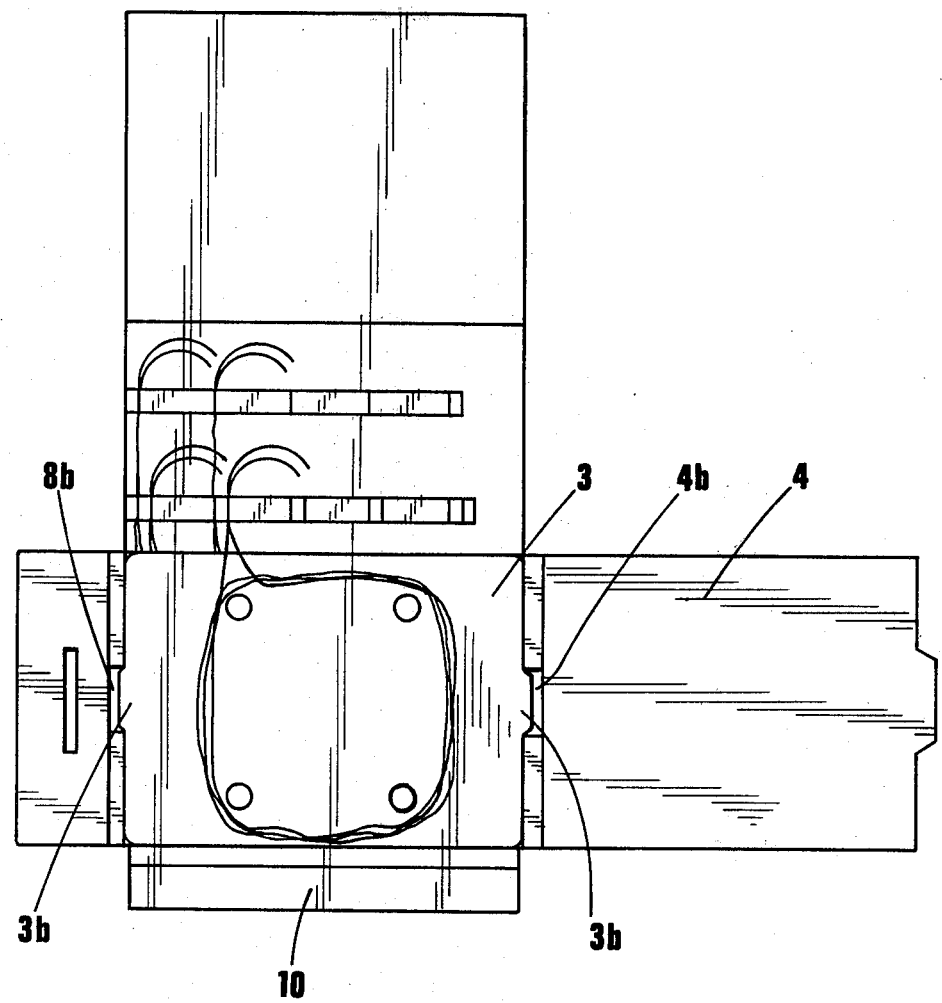
FIG. 3 is a front view of FIG. 2 shown with cards.
Figure 4:
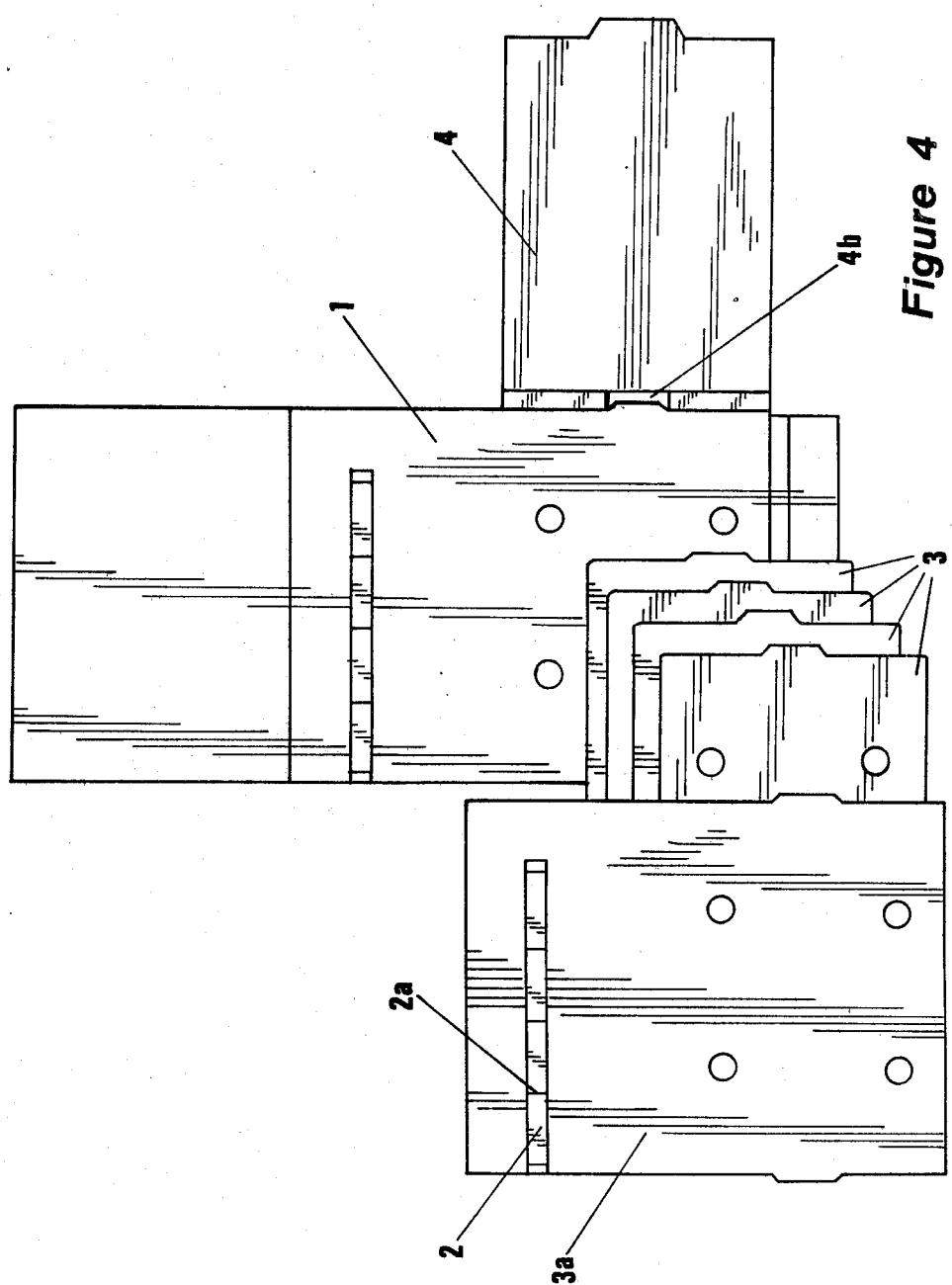
FIG. 4 is an alternative embodiment of FIG. 3 showing at least one foam receptacle affixed to a card.

FIGS. 3 and 4 describe the preferred suture package. FIG. 3 further describes the preferred suture configuration. It is to be understood that the package does not have to be opened as described in FIGS. 3 and 4 to dispense a suture from the foam receptacle 2. Also, it is to be understood that other package designs and/or suture configurations can be within the scope of this invention.

Figure 2:
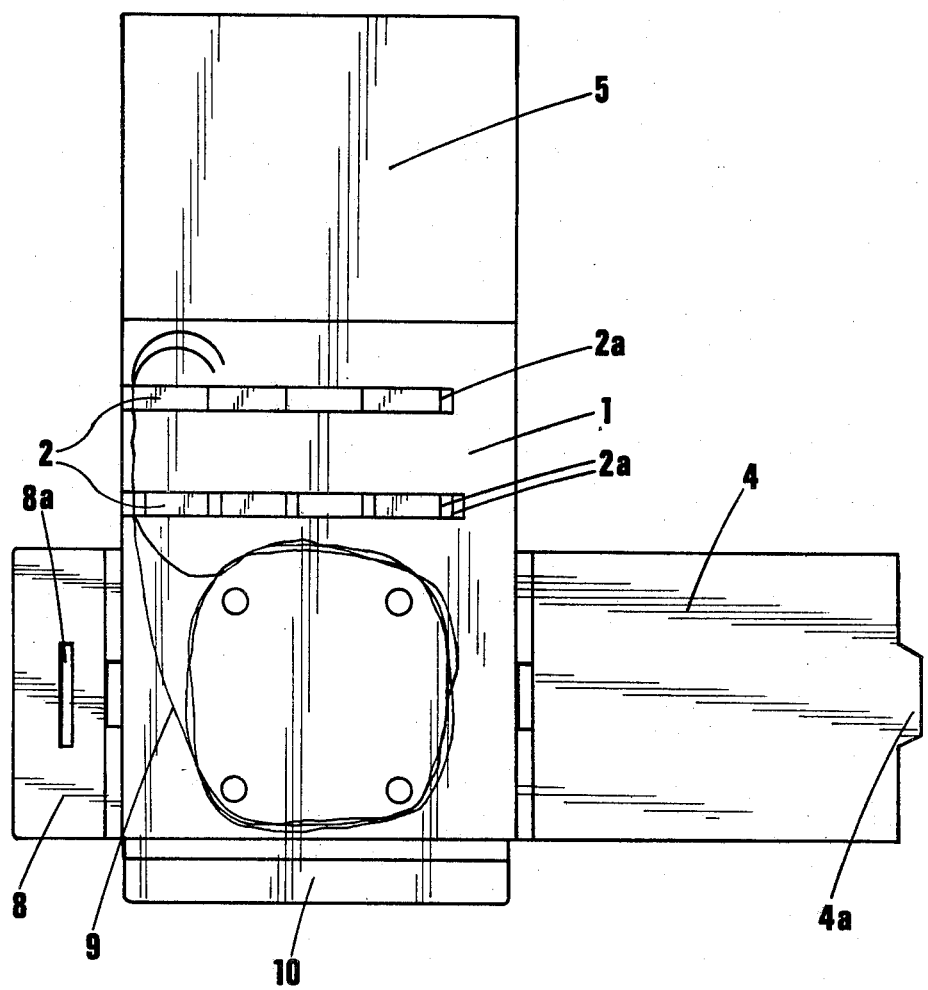
FIG. 2 is a front view of an unfolded suture package of FIG. 1 shown without cards.

Referring to FIG. 2 the package comprises a center panel 1. At least one foam receptacle 2 is affixed to the panel 1. Two foam receptacles 2 are affixed in tandem to the panel 1. A first flap 4 is adjacent to one edge of the panel 1. The first flap 4 can be foldably attached to the panel 1.

The first flap 4 is contained on the cards 3 and on the panel 1 by attaching means. When the first flap 4 is foldably attached to the panel 1, the means for attaching the first flap 4 to the panel 1 can be a tab 4a on the first flap 4, and a third flap 8 foldably attached to the panel 1. The third flap 8 contains a slot 8a. The first flap tab 4a coordinates with the third flap slot 8a.

A second flap 5 is foldably attached to the panel 1. The second flap 5 can be placed onto the receptacle or receptacles 2 and the first flap 4.

At least one end of the suture 9 is held in place by the receptacle or receptacles 2. Preferably, the receptacle or receptacles 2 contain suture mounting means, e.g. slits 2a. Other suture mounting means can be, e.g. raised portions contoured onto the receptacle or receptacles 2. Also, preferably, both ends of the suture 9 are contained in a mounting slit 2a. If two foam receptacles 2 are affixed in tandem to the panel 1 and if the ends of the suture 9 are contained in a mounting slit 2a in the distal receptacle 2, then preferably, the ends of the suture 9 are also contained in a coordinating mounting slit 2a in the proximal receptacle 2. Preferably, the first receptacle 7 is manufactured from a commercially available polyolefin foam, such as polyethylene or polypropylene. A double backed adhesive can be used to affix the foam receptacle of receptacles to the panel 1.

Referring to FIGS. 3 and 4 a plurality of cards 3 are placed on panel 1 adjacent to receptacle or receptacles 2. The attaching means can be a tab 3b on opposite edges of each card and an opening 4b and 8b on the first flap 4 and on the third flap 8, respectively. Each tab 3b on each card 3 coordinates with the respective first flap opening 4b and third flap opening 8b.

Referring more specifically to FIG. 4, an alternative embodiment of FIG. 3 is described. In FIG. 4 at least one foam receptacle 2 is affixed to a card 3a. The plurality of cards 3 and 3a are placed on panel 1 as described in FIG. 3. Also, the attaching means can be as described in FIG. 3. Although not shown, it is to be understood that a plurality of cards, the same or similar to cards 3, are contained on the card 3a containing the foam receptacle 2. A suture 9 (described in FIG. 3) is then loaded onto the card 3a and onto each of the plurality of cards which are external to the card 3a. At least one end of the suture 9 is held in place by the receptacle 2 affixed to the card 3a. Preferably, the receptacle 2 contains suture mounting means 2a.

A suture 9 is loaded onto the center panel 1 and onto each of the plurality of cards 3 in a non-tangling configuration. Preferably, the configuration is a helical, coil or figure eight configuration. Also, other coil configurations, e.g. sinusoidal, may be used provided they allow direct dispensing of the suture without tangling.

Figure 5:
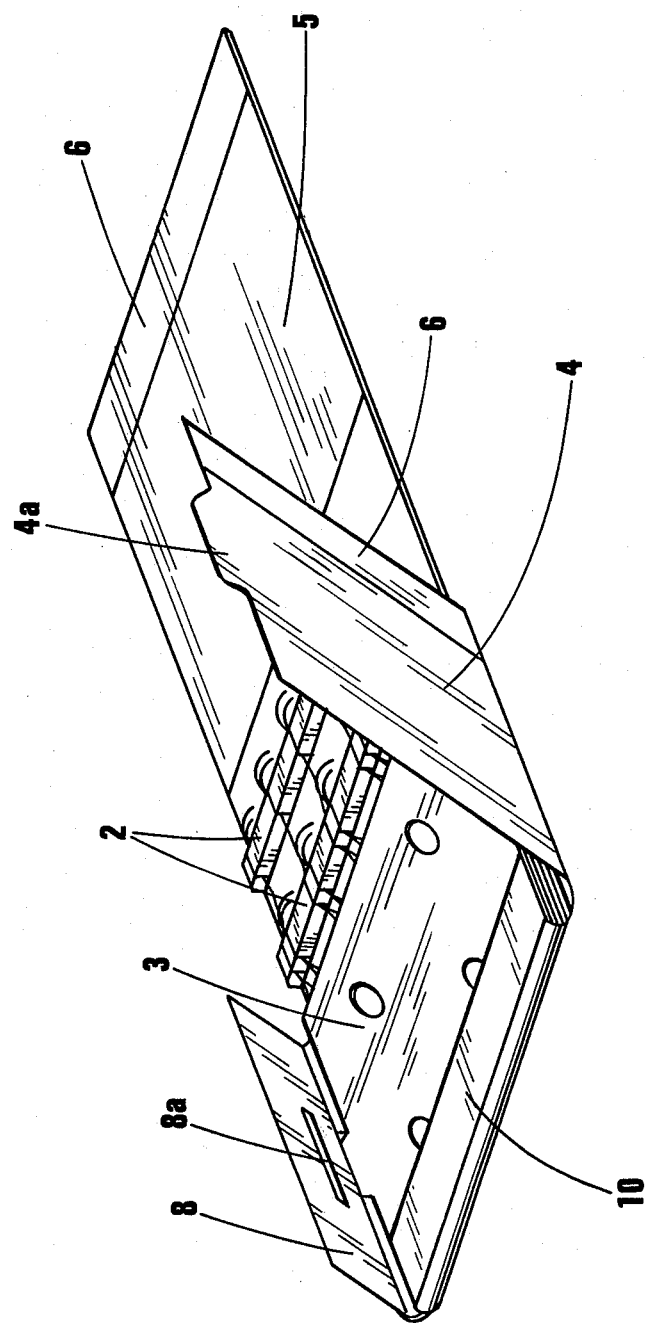
FIG. 5 is a perspective view showing the folding sequence of the suture packages of FIGS. 1, 3 and 4.

FIG. 5 describes the folding sequence of the suture package of FIGS. 2 to 4. Fourth flap 10 is optional. If used, fourth flap 10 is placed onto the plurality of cards 3. Third flap 8 is then placed onto fourth flap 10, and onto the plurality of cards 3 such that each adjacent tab 3b on each card 3 coordinates with the third flap opening 8b (more fully shown in FIG. 3). First flap 4 is then placed onto third flap 8, and onto the plurality of cards 3 such that each adjacent tab 3b on each card 3 coordinates with the first flap opening 4b (more fully shown in FIG. 3). The first flap tab 4a coordinates with the third flap slot 8a. First contacting means 6 is then placed on first and third flaps 4 and 8, respectively, as described in FIG. 5. Second flap 5 is placed onto the receptacle or receptacles 2 and onto the first flap 4. The folded package is described in FIG. 1.

Figure 6:
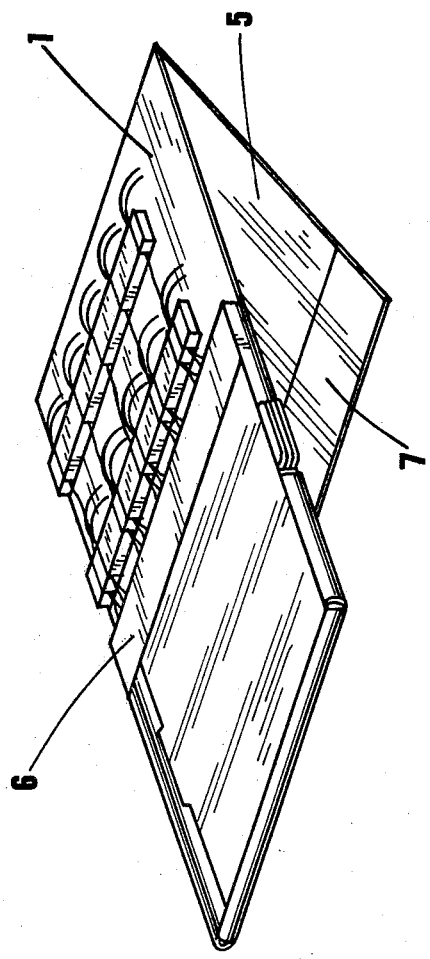
FIG. 6 is a perspective view showing the second flap rotated onto the external surface of the center panel.

Referring to FIGS. 1, 5 and 6, a first contacting means 6 can be contained on the internal surface of the second flap 5. Preferably, the first contacting means is a coordinating adhesive strip affixed to the second flap 5 and to the first flap 4. Referring specifically to FIG. 6, the second flap 5 can be rotated onto the external surface of the center panel 1. The second flap 5 can then be affixed to a suture package support, e.g. a towel or a Mayo stand, by the first contacting means 6 (more fully shown in FIG. 5).

Referring to FIGS. 1 and 6, a second contacting means 7 can be contained on the external surface of the second flap 5. Preferably, the second contacting means is a pealable adhesive strip. Referring specifically to FIG. 6, the second flap 5 can be rotated adjacent to the external surface of the center panel 1. The adhesive strip is exposed. The second flap 5 can then be affixed to the center panel 1.

I claim:

1. A surgical suture package comprising a center panel; at least one foam receptacle affixed to said panel; a plurality of cards placed onto said panel adjacent to said receptacle; a plurality of sutures each singly contained in a non-tangling configuration over a major portion of each card wherein the area surrounded by said configuration comprises an area larger than the remaining portion of the card; a first flap placed onto said cards; means for attaching said first flap to said cards and to said panel; and a second flap foldably attached to said panel and placed onto said receptacle and said first flap, whereby said sutures can be contained with at least one end of each suture contained by said receptacle.

2. A package of claim 1 wherein two foam receptacles are affixed respectively to said panel and to a card.

3. A package of claim 2 wherein said receptacles are affixed in tandem.

4. A package of claim 3 wherein said receptacles contain suture mounting means.

5. A package of claim 4 wherein said first flap is foldably attached to said panel.

6. A package of claim 5 wherein the means for attaching said first flap to said panel is a tab on said first flap and a third flap foldably attached to said panel, opposing said first flap and containing a slot, whereby said first flap tab coordinates with said third flap slot.

7. A package of claim 6 wherein the means for attaching said first flap to said cards is a tab on opposing edges of each card and an opening on the opposing edges of said first and third flaps, whereby each tab coordinates with each opening.

8. A package of claim 1 or 2 wherein each suture is single armed.

9. A package as in claims 1 or 2 or 4 wherein each suture of said plurality of sutures is double armed with the respective ends of each respective ends of each respective suture contained in a receptacle.

* * * * *